(12) United States Patent
Levy et al.

(10) Patent No.: US 9,133,518 B2
(45) Date of Patent: Sep. 15, 2015

(54) METHOD FOR DETERMINING PREDISPOSITION TO PULMONARY INFECTION

(75) Inventors: Hara Levy, Bayside, WI (US); Craig Gerard, Chestnut Hill, MA (US); Gerald Pier, Brookline, MA (US); Scott Weiss, Chestnut Hill, MA (US); Christoph Lange, Cambridge, MA (US)

(73) Assignee: Presidental and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/296,557

(22) Filed: Nov. 15, 2011

(65) Prior Publication Data

US 2012/0121593 A1     May 17, 2012

Related U.S. Application Data

(63) Continuation of application No. 12/111,064, filed on Apr. 28, 2008, now Pat. No. 8,080,394.

(60) Provisional application No. 60/926,649, filed on Apr. 27, 2007.

(51) Int. Cl.
    *C12P 19/34*     (2006.01)
    *C12Q 1/68*     (2006.01)
    *A61K 38/14*     (2006.01)

(52) U.S. Cl.
CPC .............. *C12Q 1/6883* (2013.01); *A61K 38/14* (2013.01); *C12Q 2600/106* (2013.01); *C12Q 2600/112* (2013.01); *C12Q 2600/118* (2013.01); *C12Q 2600/156* (2013.01); *C12Q 2600/158* (2013.01)

(58) Field of Classification Search
CPC ............... C12Q 1/6806; C12Q 1/6883; C12Q 2600/156; C12Q 2600/106; C12Q 2600/112; C12Q 2600/118; C12Q 2600/158
USPC ........................................................ 435/91.2
See application file for complete search history.

(56) References Cited

PUBLICATIONS

Oermann et al., Chest, vol. 114, No. 4, pp. 1053-1058, 1999.*
Prescott et al., Pharmacotherapy, vol. 25, No. 4, pp. 555-573, 2005.*
Pukhalsky et al, Mediators of Inflammation, vol. 8, pp. 159-167, 1999.
Levy et al., Proc. Am. Thorac. Soc., vol. 5, pp. 373-374, 2008.

* cited by examiner

*Primary Examiner* — Cynthia B Wilder
(74) *Attorney, Agent, or Firm* — Mintz Levin Cohn Ferris Glovsky and Popeo, P.C.; Peter F. Corless; Christopher R. Cowles

(57) ABSTRACT

Provided herein are methods and materials for diagnosing a subject's predisposition for pulmonary infection in a CF subject by detecting a pulmonary infection genetic marker. Pulmonary infection markers have been identified in the IL-1 gene cluster and may be useful in predicting CF disease progression and assessing a CF subject's response to therapy.

12 Claims, 2 Drawing Sheets

SEQUENCE LISTING

<160> NUMBER OF SEQ ID NOS: 36

<210> SEQ ID NO 1
<211> LENGTH: 201
<212> TYPE: DNA
<213> ORGANISM: Homo sapiens
<220> FEATURE:
<221> NAME/KEY: misc_feature
<222> LOCATION: (178)..(178)
<223> OTHER INFORMATION: n is a, c, g, or t

<400> SEQUENCE: 1
gaccagacat caccaagctt ttttgctgtg agtcccggag cgtgcagttc agtgatcgta        60
caggtgcatc gtgcacataa gcctcgttat cccatgtgtc aaagaagata ggttctgaaa       120
tgtggagcac atgttgttta ggtataaaat cagaagggca ggcctcgtga ggcgaggngg       180
caaaatttga tttcttggag g                                                 201

<210> SEQ ID NO 2
<211> LENGTH: 201
<212> TYPE: DNA
<213> ORGANISM: Homo sapiens
<220> FEATURE:
<221> NAME/KEY: misc_feature
<222> LOCATION: (178)..(178)
<223> OTHER INFORMATION: n is a, c, g, or t

<400> SEQUENCE: 2
gaccagacat caccaagctt ttttgctgtg agtcccggag cgtgcagttc agtgatcgta        60
caggtgcatc gtgcacataa gcctcgttat cccatgtgtc gaagaagata ggttctgaaa       120
tgtggagcac atgttgttta ggtataaaat cagaagggca ggcctcgtga ggcgaggngg       180
caaaatttga tttcttggag g                                                 201

<210> SEQ ID NO 3
<211> LENGTH: 201
<212> TYPE: DNA
<213> ORGANISM: Homo sapiens
<220> FEATURE:
<221> NAME/KEY: misc_feature
<222> LOCATION: (102)..(102)
<223> OTHER INFORMATION: n is a, c, g, or t

<400> SEQUENCE: 3
ggattgaagg ttgcacgcag ttaaaaatta tgttaaattt atttacatta atgcaaaatt        60
gtcaaataga cctgttccca gctttcctta gggatggggg tnggagaag gtggttgtct       120 gggaataagt ggtagcagga ggctgagaag ggcttcattc catagcattc acttacctcc       180
agctgtagag tgggcttatc a                                                 201

<210> SEQ ID NO 4
<211> LENGTH: 201
<212> TYPE: DNA
<213> ORGANISM: Homo sapiens
<220> FEATURE:
<221> NAME/KEY: misc_feature
<222> LOCATION: (102)..(102)
<223> OTHER INFORMATION: n is a, c, g, or t

<400> SEQUENCE: 4
ggattgaagg ttgcacgcag ttaaaaatta tgttaaattt atttacatta atgcaaaatt        60
gtcaaataga cctgttccca gctttcctta gggatggggg cnggagaag gtggttgtct       120 gggaataagt ggtagcagga ggctgagaag ggcttcattc catagcattc acttacctcc       180
agctgtagag tgggcttatc a                                               201

<210> SEQ ID NO 5
<211> LENGTH: 201
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is a, c, g, or t

<400> SEQUENCE: 5
aacttaccta ttttatttta ttttagaaat tcatcttact gcctcagaat taaaataagt    60
gcaaaatttg tggagaatga ncctaactta tgttataatg acaagccat atttaagcag    120 aaactacccg ttgcaggaga cggaggactt gtgtgcccct atatggagtt ttttaaaaat   180
gaaaataatg agttacctaa a                                              201

<210> SEQ ID NO 6
<211> LENGTH: 201
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is a, c, g, or t

<400> SEQUENCE: 6
aacttaccta ttttatttta ttttagaaat tcatcttact gcctcagaat taaaataagt    60
gcaaaatttg tggagaatga ncctaactta tgttataatg cacaagccat atttaagcag   120
aaactacccg ttgcaggaga cggaggactt gtgtgcccct atatggagtt ttttaaaaat   180
gaaaataatg agttacctaa a                                              201

<210> SEQ ID NO 7
<211> LENGTH: 201
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t

<400> SEQUENCE: 7
gctcgaatta tactttgatt gagggcgtna ttcaggatga attcgtattt gatgatcctc    60
ataaagtngt atttcacatt gctcaggaag ctaaaaggtg atgacctagg cttgatgatt   120
tctaaaacca tgatcacaag tgcagattaa tgtctatgta caaacacaga tgatatacac   180
agtctagtac aaacagggaa a                                              201

<210> SEQ ID NO 8
<211> LENGTH: 201
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (68)..(68)

```
<223> OTHER INFORMATION: n is a, c, g, or t

<400> SEQUENCE: 8
gctcgaatta actttgatt gagggcgtna ttcaggatga attcgtattt gatgatcctc    60
ataaagtngt atttcacatt gctcaggaag ctaaaaggtg ctgacctagg cttgatgatt   120
tctaaaacca tgatcacaag tgcagattaa tgtctatgta caaacacaga tgatatacac   180
agtctagtac aaacagggaa a                                             201

<210> SEQ ID NO 9
<211> LENGTH: 201
<212> TYPE: DNA
<213> ORGANISM: Homo sapiens
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t

<400> SEQUENCE: 9
taaagaaata tgtttttaac aagattgagg actggattat gaggctaggg gaggctatca    60
caaactggaa taaataaag ccagagaaaa gtggctgcnt cccaacctgc acaactgacc    120
tagctaggct gatggctggg ccnnctagga aggctactga gcatcatata aaacagaagg   180
gacagcagga atataacatg g                                             201

<210> SEQ ID NO 10
<211> LENGTH: 201
<212> TYPE: DNA
<213> ORGANISM: Homo sapiens
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t

<400> SEQUENCE: 10
taaagaaata tgtttttaac aagattgagg actggattat gaggctaggg gaggctatca    60
caaactggaa taaataaag ccagagaaaa gtggctgcnt tccaacctgc acaactgacc    120
tagctaggct gatggctggg ccnnctagga aggctactga gcatcatata aaacagaagg   180
gacagcagga atataacatg g                                             201

<210> SEQ ID NO 11
<211> LENGTH: 201
<212> TYPE: DNA
<213> ORGANISM: Homo sapiens
<220> FEATURE:
<221> NAME/KEY: misc_feature
<222> LOCATION: (24)..(24)
<223> OTHER INFORMATION: n is a, c, g, or t

<400> SEQUENCE: 11
taagcctcgt tatcccatgt gtcnaagaag ataggttctg aaatgtggag cacatgttgt    60
ttaggtataa aatcagaagg gcaggcctcg tgaggcgagg tggcaaaatt tgatttcttg   120
gaggacacct gagcatatac ggtcaaagtc tgatgacaac accagtaggg atgaagctgg   180
gagtggggtg gctaagaaca c                                             201
```

<210> SEQ ID NO 12
<211> LENGTH: 201
<212> TYPE: DNA
<213> ORGANISM: Homo sapiens
<220> FEATURE:
<221> NAME/KEY: misc_feature
<222> LOCATION: (24)..(24)
<223> OTHER INFORMATION: n is a, c, g, or t

<400> SEQUENCE: 12

```
taagcctcgt tatcccatgt gtcnaagaag ataggttctg aaatgtggag cacatgttgt      60
ttaggtataa aatcagaagg gcaggcctcg tgaggcgagg cggcaaaatt tgatttcttg     120
gaggacacct gagcatatac ggtcaaagtc tgatgacaac accagtaggg atgaagctgg     180
gagtggggtg gctaagaaca c                                              201
```

<210> SEQ ID NO 13
<211> LENGTH: 201
<212> TYPE: DNA
<213> ORGANISM: Homo sapiens

<400> SEQUENCE: 13

```
tctgtcttcc agaccacgta tgctttcctc cacctttgca tcttttatct tctgccagcc      60
cagatgcttg ctgactccag cccaagccta taggataagc tacagcctgt ccctacagac     120
tacgcattgc agaatctaag acatcaagtc aagttcggaa gcacttgcct tctcctctcc     180
aggtacacag gctctcctgg a                                              201
```

<210> SEQ ID NO 14
<211> LENGTH: 201
<212> TYPE: DNA
<213> ORGANISM: Homo sapiens

<400> SEQUENCE: 14

```
tctgtcttcc agaccacgta tgctttcctc cacctttgca tcttttatct tctgccagcc      60
cagatgcttg ctgactccag cccaagccta taggataagc cacagcctgt ccctacagac     120
tacgcattgc agaatctaag acatcaagtc aagttcggaa gcacttgcct tctcctctcc     180
aggtacacag gctctcctgg a                                              201
```

<210> SEQ ID NO 15
<211> LENGTH: 199
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

<400> SEQUENCE: 15

```
ggattattcc aaaaagagcc tcaacatgca ggcgcttatt atnacttctc ttgcatcatc      60
ctattggcca aagccagtca ngtggctaag tctagcccct tgtgagagga gactncataa     120
gagtgtgaac accaggagac acggtcactg gggccaccac tgtaaccatc taccacagga     180
```
cctgaatctc tgtgtgcta                                                        199

<210> SEQ ID NO 16
<211> LENGTH: 199
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

<400> SEQUENCE: 16
ggattattcc aaaaagagcc tcaacatgca ggcgcttatt atnacttctc ttgcatcatc     60
ctattggcca aagccagtca ngtggctaag tctagccccc tgtgagagga gactncataa    120
gagtgtgaac accaggagac acggtcactg gggccaccac tgtaaccatc taccacagga    180
cctgaatctc tgtgtgcta                                                 199

<210> SEQ ID NO 17
<211> LENGTH: 201
<212> TYPE: DNA
<213> ORGANISM: Homo sapiens
<220> FEATURE:
<221> NAME/KEY: misc_feature
<222> LOCATION: (88)..(88)
<223> OTHER INFORMATION: n is a, c, g, or t

<400> SEQUENCE: 17
atgatcacaa gtgcagatta atgtctatgt acaaacacag atgatataca cagtctagta     60
caaacaggga aaatagttct ggaggggnta ttaggaatat gccaatccag atgaggaagc    120
aaagagaagt gaaatcaccc agtcagcaga actggttttc taggattatc cttgttgttg    180
cttatgtgct tcttttttaaa c                                             201

<210> SEQ ID NO 18
<211> LENGTH: 201
<212> TYPE: DNA
<213> ORGANISM: Homo sapiens
<220> FEATURE:
<221> NAME/KEY: misc_feature
<222> LOCATION: (88)..(88)
<223> OTHER INFORMATION: n is a, c, g, or t

<400> SEQUENCE: 18
atgatcacaa gtgcagatta atgtctatgt acaaacacag atgatataca cagtctagta     60
caaacaggga aaatagttct ggaggggnta ttaggaatat ccaatccag atgaggaagc     120 aaagagaagt gaaatcaccc agtcagcaga actggttttc taggattatc cttgttgttg    180
cttatgtgct tcttttttaaa c                                             201

<210> SEQ ID NO 19
<211> LENGTH: 28
<212> TYPE: DNA
<213> ORGANISM: Homo sapiens

<400> SEQUENCE: 19
acgttggatg agacctgttc ccagcttc                                        28

<210> SEQ ID NO 20
<211> LENGTH: 29
<212> TYPE: DNA
<213> ORGANISM: Homo sapiens

<400> SEQUENCE: 20
acgttggatg ctcctgctac cacttattc                                    29

<210> SEQ ID NO 21
<211> LENGTH: 28
<212> TYPE: DNA
<213> ORGANISM: Homo sapiens

<400> SEQUENCE: 21
acgttggatg gtgctccaca tttcagac                                     28

<210> SEQ ID NO 22
<211> LENGTH: 29
<212> TYPE: DNA
<213> ORGANISM: Homo sapiens

<400> SEQUENCE: 22
acgttggatg cagttcagtg atcgtacag                                    29

<210> SEQ ID NO 23
<211> LENGTH: 28
<212> TYPE: DNA
<213> ORGANISM: Homo sapiens

<400> SEQUENCE: 23
acgttggatg ctcctgcaac gggtagtc                                     28

<210> SEQ ID NO 24
<211> LENGTH: 29
<212> TYPE: DNA
<213> ORGANISM: Homo sapiens

<400> SEQUENCE: 24
acgttggatg gtgcaaaatt tgtggagag                                    29

<210> SEQ ID NO 25
<211> LENGTH: 28
<212> TYPE: DNA
<213> ORGANISM: Homo sapiens

<400> SEQUENCE: 25
acgttggatg tttcacattg ctcaggac                                     28

<210> SEQ ID NO 26
<211> LENGTH: 29
<212> TYPE: DNA
<213> ORGANISM: Homo sapiens

<400> SEQUENCE: 26
acgttggatg atctgcactt gtgatcatg                                    29

<210> SEQ ID NO 27
<211> LENGTH: 28
<212> TYPE: DNA
<213> ORGANISM: Homo sapiens

<400> SEQUENCE: 27
acgttggatg tgaccgtata tgctcagg                                           28

<210> SEQ ID NO 28
<211> LENGTH: 29
<212> TYPE: DNA
<213> ORGANISM: Homo sapiens

<400> SEQUENCE: 28
acgttggatg ataaaatcag aagggcagc                                          29

<210> SEQ ID NO 29
<211> LENGTH: 28
<212> TYPE: DNA
<213> ORGANISM: Homo sapiens

<400> SEQUENCE: 29
acgttggatg gcttgcatca tcctattc                                           28

<210> SEQ ID NO 30
<211> LENGTH: 29
<212> TYPE: DNA
<213> ORGANISM: Homo sapiens

<400> SEQUENCE: 30
acgttggatg ctggtgttca cactcttag                                          29

<210> SEQ ID NO 31
<211> LENGTH: 28
<212> TYPE: DNA
<213> ORGANISM: Homo sapiens

<400> SEQUENCE: 31
acgttggatg tgactgggtg atttcacc                                           28

<210> SEQ ID NO 32
<211> LENGTH: 29
<212> TYPE: DNA
<213> ORGANISM: Homo sapiens

<400> SEQUENCE: 32
acgttggatg gggaaaatag ttctggagg                                          29

<210> SEQ ID NO 33
<211> LENGTH: 28
<212> TYPE: DNA
<213> ORGANISM: Homo sapiens

<400> SEQUENCE: 33
acgttggatg cttttatctt ctgccagc                                           28

<210> SEQ ID NO 34
<211> LENGTH: 29
<212> TYPE: DNA
<213> ORGANISM: Homo sapiens

<400> SEQUENCE: 34
acgttggatg tgcaatgcgt agtctgtag                                          29

<210> SEQ ID NO 35
<211> LENGTH: 28
<212> TYPE: DNA
<213> ORGANISM: Homo sapiens

<400> SEQUENCE: 35

```
acgttggatg cttttatctt ctgccagc                                28

<210> SEQ ID NO 36
<211> LENGTH: 29
<212> TYPE: DNA
<213> ORGANISM: Homo sapiens

<400> SEQUENCE: 36
acgttggatg tgcaatgcgt agtctgtag                               29
```

METHOD FOR DETERMINING PREDISPOSITION TO PULMONARY INFECTION

CROSS-RELATED APPLICATIONS

This is a continuation of U.S. patent application Ser. No. 12/111,064, filed on Apr. 28, 2008, now U.S. Pat. No. 8,080,394 which claims the benefit of U.S. provisional patent application No. 60/926,649, filed on Apr. 27, 2007, the contents of all of which are incorporated by reference in their entirety.

FEDERALLY SPONSORED RESEARCH

This invention was made with government support under NHLBI K23 grant number K23HL074202. The government has certain rights in the invention.

FIELD OF THE INVENTION

The present invention relates to the IL-1 gene family and its association with lung disease in cystic fibrosis patients.

BRIEF DESCRIPTION OF SEQUENCE LISTING

Applicant hereby makes reference to the Sequence Listing, which is contained in the file named "SequenceListing.txt" (11.2 Kb, created Dec. 12, 2011), the contents of which are incorporated herein by reference.

BACKGROUND

Progressive pulmonary disease associated with chronic bacterial infection and airway inflammation is the major cause of morbidity and mortality in cystic fibrosis (CF) patients. CF lung disease may be characterized by chronic bacterial infection, with prevalence of infection increasing with age. CF patients with the most common CF transmembrane conductance regulator (CFTR) mutation, ΔF508, a deletion of a phenylalanine at position F508 of CFTR, often have markedly different clinical courses; some have less aggressive lung disease and survive into their 50s, while others have a precipitous decline in lung function and die of respiratory failure in their early 20s. What accounts for this phenotypic heterogeneity is unclear.

Early assessment of lung disease severity may present the best opportunity for treatment intervention. With the development of genetic testing, it is possible to identify genetic markers that will be indicative of a propensity to develop disease or indicative of a disease state. There remains a need to identify one or more genetic markers that are associated with lung disease in CF patients. These genetic markers may represent allelic variants, which may be useful in diagnosing lung disease severity, and whose products may be targeted for early intervention therapy.

SUMMARY OF THE INVENTION

Provided herein is a method for determining a CF subject's predisposition for pulmonary infection. The method may comprise providing a nucleic acid-containing sample from a cystic fibrosis patient. A determination may be made as to whether the sample comprises a pulmonary infection marker. The pulmonary infection marker may be in an IL-1 gene cluster. The IL-1 gene cluster may comprise the genes IL-1α, IL-1RN, IL-1R1, and IL-1β. The presence of a pulmonary infection marker ("PI-marker") may indicate that the subject has a predisposition for pulmonary infection. The marker may be a SNP as shown in $rs1143639^{256T}$ (SEQ ID NO:3), wherein the SNP corresponds to nucleotide 256 of SEQ ID NO:3 and is a thymine; $rs1143639^{256C}$ (SEQ ID NO:4), wherein the SNP corresponds to nucleotide 256 of SEQ ID NO:4 and is a cytosine; $rs1143634^{401A}$ (SEQ ID NO:1), wherein the SNP corresponds to nucleotide 401 of SEQ ID NO:1 and is an adenine; $rs1143634^{401G}$ (SEQ ID NO:2), wherein the SNP corresponds to nucleotide 401 of SEQ ID NO:2 and is a guanine; $rs2228139^{301G}$ (SEQ ID NO:5), wherein the SNP corresponds to nucleotide 301 of SEQ ID NO:5 and is a guanine; $rs2228139^{301C}$ (SEQ ID NO:6), wherein the SNP corresponds to nucleotide 301 of SEQ ID NO:6 and is a cytosine; $rs17561^{256A}$ (SEQ ID NO:7), wherein the SNP corresponds to nucleotide 256 of SEQ ID NO:7 and is an adenine; $rs17561^{256C}$ (SEQ ID NO:8), wherein the SNP corresponds to nucleotide 256 of SEQ ID NO:8 and is a cytosine; $rs3917356^{256C}$ (SEQ ID NO:9), wherein the SNP corresponds to nucleotide 256 of SEQ ID NO:9 and is a cytosine; $rs3917356^{256T}$ (SEQ ID NO:10), wherein the SNP corresponds to nucleotide 256 of SEQ ID NO:10 and is a thymine; $rs1143633^{401T}$ (SEQ ID NO:11), wherein the SNP corresponds to nucleotide 401 of SEQ ID NO:11 and is a thymine; $rs1143633^{401C}$ (SEQ ID NO:12), wherein the SNP corresponds to nucleotide 401 of SEQ ID NO:12 and is a cytosine; $rs3917368^{301T}$ (SEQ ID NO:13), wherein the SNP corresponds to nucleotide 301 of SEQ ID NO:13 and is a thymine; $rs3917368^{301C}$ (SEQ ID NO:14), wherein the SNP corresponds to nucleotide 301 of SEQ ID NO:14 and is a cytosine; $rs4252019^{501T}$ (SEQ ID NO:15), wherein the SNP corresponds to nucleotide 501 of SEQ ID NO:15 and is a thymine; $rs4252019^{501C}$ (SEQ ID NO:16), wherein the SNP corresponds to nucleotide 501 of SEQ ID NO:16 and is a cytosine; $rs2071374^{301G}$ (SEQ ID NO:17), wherein the SNP corresponds to nucleotide 301 of SEQ ID NO:17 and is a guanine; and $rs2071374^{301T}$ (SEQ ID NO:18), wherein the SNP corresponds to nucleotide 301 of SEQ ID NO:18 and is a thymine. The marker may be amplified. Amplification of a marker may be via polymerase chain reaction and primers. The marker may be detected by sequence analysis or oligonucleotide probe hybridization. The oligonucleotide probe may be labeled. The oligonucleotide may consist of a sequence selected from the group of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18, or a fragment thereof.

A marker may indicate a subject's predisposition to severe pulmonary infection. The pulmonary infection, whether severe or mild, may be associated with bacterial lung colonization. The infection may be caused by *Pseudomonas aeruginosa*. A PI-marker associated with severe pulmonary infection may be $rs3917356^{256C}$, $rs1143633^{401T}$, $rs4252019^{501T}$, and/or $rs1143639^{256T}$. A marker may indicate a subject's predisposition to mild pulmonary infection. Such a marker may be $rs2071374^{301G}$. A marker may be common in one geographical, ethnic, gender, and/or age group, and may be more rare, or non-existent, in another. The marker $rs2228139^{301G}$ and/or $rs1143634^{401A}$ may indicate a female subject's predisposition to severe lung infection. The marker $rs17561^{256A}$ may indicate a male subject's predisposition to severe lung infection. Severe lung infection may be further associated with an adjusted forced expiratory volume in 1 second ($FEV_1$). The $FEV_1$ may be a value percentage higher or lower than a predicted percentage for a control subject. The $FEV_1$ may be adjusted according to geographical data, ethnicity, gender, and/or age of the subject being tested. Severe lung disease or lung infection may be associated with *Pseudomonas aeruginosa* lung colonization.

Also provided herein is a method of treating a subject identified as having a predisposition to pulmonary lung infection and/or lung disease. The subject may have an $FEV_1$ value that is lower than a predicted percentage for a control subject. The $FEV_1$ may be adjusted according to geographical data, ethnicity, gender, and/or age of the subject being tested. The subject may have pulmonary infection associated with *Pseudomonas aeruginosa* lung colonization. The method may comprise administering an anti-infection agent to the subject. The anti-infection agent may be an anti-inflammatory agent or an antibacterial agent. The anti-inflammatory agent may be an IL-1 blocker such as rilonacept, anakinra, and/or Zn-protoporphyrin (ZnPP). The antibacterial agent may be an antibiotic such as an aminoglycoside, amoxicillin, levofloxacin, dicloxacillin, cephalexin, amoxicillin/clavulanate, erythromycin, clarithromycin, azithromycin, clindamycin, cefuroxime axetil, cefprozil, cefixime, cefpodoxime proxetil, loracarbef, ciprofloxacin, tobramycin, colistin, trimethoprim/sulfamethoxazole, doxycycline, minocycline, cefazolin, nafcillin, vancomycin, β-lactam, ceftazidime, ticarcillin, piperacillin, imipenem, meropenem, aztreonam, an aminoglycoside, amikacin, merpenem, ceftazidime, chloramphenicol, ticarcillin/clavulanate, aztreonam, imipenem, a polypeptide antibiotic, and/or meropenem. The polypeptide antibiotic may be of the polymyxin class of antibiotics.

Also provided herein is a kit for performing a method for diagnosing severity of lung disease in a CF patient. The kit may comprise a means for collecting a DNA sample, a means for detecting a SNP in an allele, a control sample, and instructions for performing the method of diagnosis. The control sample may comprise nucleic acid selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

DETAILED DESCRIPTION

Figure 1:
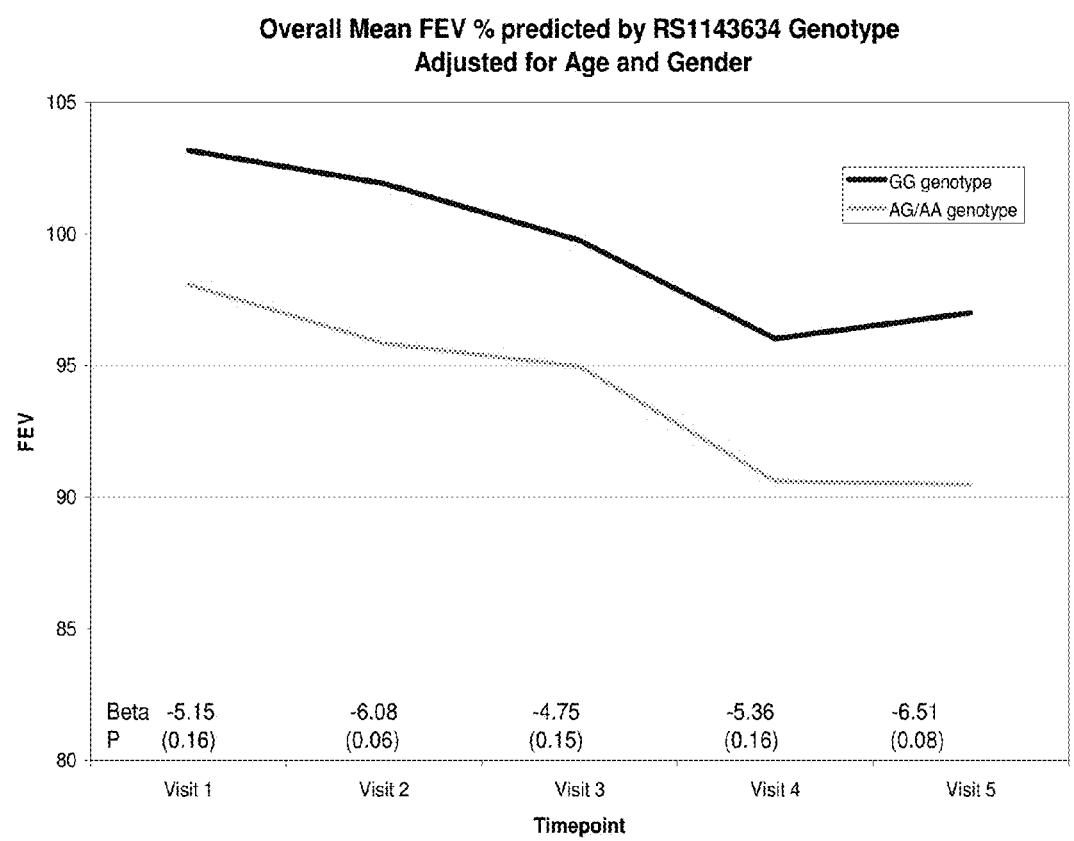
FIG. 1 shows the overall mean FEV % predicted by rs1143634 genotype as adjusted for age and gender.

The inventors have made the surprising discovery that there is an association between pulmonary infection in CF patients and certain genetic markers. These genetic markers, or PI-markers, have been identified in the IL-1 gene cluster. The identification of a PI-marker in a CF subject may be useful in predicting CF disease progression and assessing the CF subject's response to therapy. In addition, knowledge of a particular marker associated with a susceptibility to developing an infection or a disease may allow one to customize the prevention or treatment in accordance with the subject's genetic profile. A comparison of a subject's IL-1 profile to a population profile for any particular disorder may permit the selection or design of drugs or other therapeutic regimens that are expected to be safe and efficacious for a particular subject or subject population. Early detection of a PI-marker may allow the subject to delay or prevent bacterial infection. A CF subject who has a PI-marker may be treated with an antibiotic and/or anti-inflammatory regimen.

The ability to target populations expected to show the highest clinical benefit, based on genetic profile, may enable the repositioning of already marketed drugs, the rescue of drug candidates whose clinical development has been discontinued as a result of safety or efficacy limitations, which may be patient sub-group-specific, and/or an accelerated and less costly development of candidate therapeutics.

The methods and materials described below use genetic analysis to determine the presence of a PI-marker and reveal whether a CF subject may be predisposed to pulmonary infection.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Fragment

"Fragment" as used herein may mean a portion of a reference peptide or polypeptide or nucleic acid sequence.

b. Identical

"Identical" or "identity" as used herein in the context of two or more polypeptide or nucleotide sequences, may mean that the sequences have a specified percentage of residues or nucleotides that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

c. Label

"Label" or "detectable label" as used herein may mean a moiety capable of generating a signal that allows the direct or indirect quantitative or relative measurement of a molecule to which it is attached. The label may be a solid such as a microtiter plate, particle, microparticle, or microscope slide; an enzyme; an enzyme substrate; an enzyme inhibitor; coenzyme; enzyme precursor; apoenzyme; fluorescent substance; pigment; chemiluminescent compound; luminescent substance; coloring substance; magnetic substance; or a metal particle such as gold colloid; a radioactive substance such as $^{125}I$, $^{131}I$, $^{32}P$, $^{3}H$, $^{35}S$, or $^{14}C$; a phosphorylated phenol derivative such as a nitrophenyl phosphate, luciferin derivative, or dioxetane derivative; or the like. The enzyme may be a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyases; an isomerase; or a ligase. The enzyme may also be conjugated to another enzyme.

The enzyme may be detected by enzymatic cycling. For example, when the detectable label is an alkaline phosphatase, a measurement may be made by observing the fluorescence or luminescence generated from a suitable substrate, such as an umbelliferone derivative. The umbelliferone derivative may comprise 4-methyl-umbellipheryl phosphate.

The fluorescent or chemiluminescent label may be a fluorescein isothiocyanate; a rhodamine derivative such as rhodamine B isothiocyanate or tetramethyl rhodamine isothiocyanate; a dancyl chloride (5-(dimethylamino)-1-naphtalenesulfonyl chloride); a dancyl fluoride; a fluorescamine(4-phenylspiro[furan-2(3H); 1ÿ-(3ÿH)-isobenzofuran]-3;3ÿ-dione); a phycobiliprotein such as a phycocyanine or physoerythrin; an acridinium salt; a luminol compound such as lumiferin, luciferase, or aequorin; imidazoles; an oxalic acid ester; a chelate compound of rare earth elements such as europium (Eu), terbium (Tb) or samarium (Sm); or a coumarin derivative such as 7-amino-4-methylcoumarin.

The label may also be a hapten, such as adamantine, fluoroscein isothiocyanate, or carbazole. The hapten may allow the formation of an aggregate when contacted with a multivalent antibody or (strep)avidin containing moiety. The hapten may also allow easy attachment of a molecule to which it is attached to a solid substrate.

The label may be detected by quantifying the level of a molecule attached to a detectable label, such as by use of electrodes; spectrophotometric measurement of color, light, or absorbance; or visual inspection.

d. Linkage Disequilibrium

"Linkage disequilibrium" as used herein may mean the co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium."

e. Minor Allele Frequency

"Minor allele frequency" as used herein may mean the lowest allele frequency at a locus that is observed in a particular population.

f. Substantially Identical

"Substantially identical," as used herein may mean that a first and second protein or nucleotide sequence are at least 50%-99% identical over a region of 8-100 or more amino acids nucleotides.

2. Method of Diagnosis

Provided herein is a method of determining a CF subject's predisposition for pulmonary infection. This predisposition may be associated with a genetic marker. The detection of a marker in a nucleic acid-containing sample from the subject may be indicative of a predisposition for infection. The pulmonary infection may be a bacterial infection. The bacteria causing the infection may be *P. aeruginosa, S. aureus, H. influenzae, B. cepacia*, methicillin-resistant *S. aureus, S. maltophilia*, or *A. xylosoxidans*. The pulmonary infection may be a non-bacterial infection. The non-bacterial infection may be a viral infection.

The pulmonary infection may be severe or mild as defined by the lowest or highest quartile of forced expired volume in 1 second ($FEV_1$) for age. $FEV_1$ may be determined by standard spirometry. Absolute values may be converted to a percentage of the predicted volume expected for a healthy individual of the same age, sex, and height on the basis of regression equations. A subject having severe pulmonary infection may have a change in an adjusted $FEV_1$ value of greater than 10% than the predicted value for a subject of the same ethnicity, age, sex, and/or height. A decrease of 10%, 11%, 12%, 13%, 14%, or 15% below the predicted value may indicate severe pulmonary infection. A decrease of between 0.1% and 9.9% below the predicted value may indicate mild or moderate pulmonary infection. $FEV_1$ values may be assigned a disease severity group using the Epidemiological Study of Cystic Fibrosis (ESCF) classification for patients in different age groups. In combination with, or independent of, $FEV_1$ values, pulmonary infection severity may be categorized based upon bacterial colonization of sputum cultures obtained from the CF subject.

a. Subject

The subject may be a human. The human may be diagnosed with cystic fibrosis. The cystic fibrosis may result from any mutation in the cystic fibrosis transmembrane conductance regulator (CFTR). The mutation may be a deletion of phenylalanine at position 508 of the CFTR (ΔF508), the result of a three base pair deletion in the genetic code. The ΔF508 mutation may result in a CFTR protein capable of conducting chloride, but either absent from the plasma membrane or insufficiently anchored in the plasma membrane because of aberrant intracellular processing. Cystic fibrosis may develop in a ΔF508 heterozygote genetic carrier subject with varying severity level and may also develop at an advanced age.

b. Sample

The sample may comprise nucleic acid from the subject. The nucleic acid may be DNA or RNA. The nucleic acid may be genomic. The sample may be used directly as obtained from the subject or following pretreatment to modify a character of the sample. Pretreatment may include extraction, concentration, inactivation of interfering components, and/or the addition of reagents.

Any cell type, tissue, or bodily fluid may be utilized to obtain a nucleic acid sample. Such cell types, tissues, and fluid may include sections of tissues such as biopsy and autopsy samples, frozen sections taken for histologic purposes, blood, plasma, serum, sputum, stool, tears, mucus, saliva, hair, and skin. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose. Archival tissues, such as those having treatment or outcome history, may also be used. Nucleic acid purification may not be necessary.

c. PI-Marker

The PI-marker may be a genetic marker. The marker may be a deletion, substitution, insertion, or a polymorphism. The polymorphism may be a single nucleotide polymorphism (SNP). The marker may be in an IL-1 gene cluster. The IL-1 gene cluster may include the nucleic acid at or near the 2q13 region of human chromosome 2. The IL-1 gene cluster may comprise the IL-1α gene, IL-1β gene, IL-1 receptor gene, and/or IL-1 receptor antagonist gene. The marker may be detected in the IL-1α gene (gene accession number X03833), IL-1β gene (gene accession number X04500), IL-1 receptor gene (gene accession number locus link ID 3554; OMIM 147810, Chromosome 2q12), or IL-1 receptor antagonist gene (gene accession number X64532).

Within a population, a marker may be assigned a minor allele frequency. There may be variations between subject populations. A marker that is common in one geographical or ethnic group may be more rare in another. The marker may be overrepresented or underrepresented in a group of CF subjects. CF subjects may be divided into groups on the basis of age, sex/gender, and/or race.

The marker may be detected as a SNP shown in rs1143639$^{256T}$ (SEQ ID NO:3), wherein nucleotide 256 of SEQ ID NO:3 is a thymine; rs1143639$^{256C}$ (SEQ ID NO:4), wherein nucleotide 256 of SEQ ID NO:4 is a cytosine; rs1143634$^{401A}$ (SEQ ID NO:1), wherein nucleotide 401 of SEQ ID NO:1 is an adenine; rs1143634$^{401G}$ (SEQ ID NO:2), wherein nucleotide 401 of SEQ ID NO:2 is a guanine; rs2228139$^{301G}$ (SEQ ID NO:5), wherein nucleotide 301 of SEQ ID NO:5 is a guanine; rs2228139$^{301C}$ (SEQ ID NO:6), wherein nucleotide 301 of SEQ ID NO:6 is a cytosine; rs17561$^{256A}$ (SEQ ID NO:7), wherein nucleotide 256 of SEQ ID NO:7 is an adenine; rs17561$^{256C}$ (SEQ ID NO:8), wherein nucleotide 256 of SEQ ID NO:8 is a cytosine; rs3917356$^{256C}$ (SEQ ID NO:9), wherein nucleotide 256 of SEQ ID NO:9 is a cytosine; rs3917356$^{256T}$ (SEQ ID NO:10), wherein nucleotide 256 of SEQ ID NO:10 is a thymine; rs1143633$^{401T}$ (SEQ ID NO:11), wherein nucleotide 401 of SEQ ID NO:11 is a thymine; rs1143633$^{401C}$ (SEQ ID NO:12), wherein nucleotide 401 of SEQ ID NO:12 is a cytosine; rs3917368$^{301T}$ (SEQ ID NO:13), wherein nucleotide 301 of SEQ ID NO:13 is a thymine; rs3917368$^{301C}$ (SEQ ID NO:14), wherein nucleotide 301 of SEQ ID NO:14 is a cytosine; rs4252019$^{501T}$ (SEQ ID NO:15), wherein nucleotide 501 of SEQ ID NO:15 is a thymine; rs4252019$^{501C}$ (SEQ ID NO:16), wherein nucleotide 501 of SEQ ID NO:16 is a cytosine; rs2071374$^{301G}$ (SEQ ID NO:17), wherein nucleotide 301 of SEQ ID NO:17 is a guanine; and rs2071374$^{301T}$ (SEQ ID NO:18), wherein nucleotide 301 of SEQ ID NO:18 is a thymine; or a fragment thereof. See Table 1. The fragment may be between 10 and 500 nucleotides, between 50 and 400 nucleotides, between 100 and 300 nucleotides, between 200 and 250 nucleotides, between 10 and 50 nucleotides, between 10 and 20 nucleotides, between 10 and 30 nucleotides, or between 10 and 40 nucleotides in length.

TABLE 1

IL-1 Gene Cluster PI-Markers ([Minor allele/Major allele])

| Sequence | dbSNP accession no. | SEQ ID NO. |
|---|---|---|
| GACCAGACATCACCAAGCTTTTTTGCTGTGAGTCCCG GAGCGTGCAGTTC AGTGATCGTACAGGTGCATCGTGCACATAAGCCTCGT TATCCCATGTGTC [A/G] AAGAAGATAGGTTCTGAAATGTGGAGCACATGTTGTT TAGGTATAAAATC AGAAGGGCAGGCCTCGTGAGGCGAGGNGGCAAAATTT GATTTCTTGGAGG | rs1143634 chr2: 113306 521- 113306721 | 1 (Minor Allele) 2 (Major Allele) |
| GGATTGAAGGTTGCACGCAGTTAAAAATTATGTTAAA TTTATTTACATTA ATGCAAAATTGTCAAATAGACCTGTTCCCAGCTTTTC CTAGGGATGGGGG [T/C] NGGGAGAAGGTGGTTGTCTGGGAATAAGTGGTAGCAG GAGGCTGAGAAGG GCTTCATTCCATAGCATTCACTTACCTCCAGCTGTAG AGTGGGCTTATCA | rs1143639 chr2: 113304 924- 113305124 | 3 (Minor Allele) 4 (Major Allele) |
| AACTTACCTATTTTATTTTATTTTAGAAATTCATCTT ACTGCCTC AGAATTAAAATAAGTGCAAAATTTGTGGAGAATGANC CTAACTTA TGTTATAATG [G/C] ACAAGCCATATTTAAGCAGAAACTACCCGTTGCAGGA GACGGAGGA CTTGTGTGCCCTTATATGGAGTTTTTTAAAAATGAAA ATAATGAGT TACCTAAA | rs2228139 | 5 (Minor Allele) 6 (Major Allele) |
| GCTCGAATTATACTTTGATTGAGGGCGTNATTCAGGA TGAATTCGT ATTTGATGATCCTCATAAAGTNGTATTTCACATTGCT CAGGAAGCT AAAAGGTG [A/C] TGACCTAGGCTTGATGATTTCTAAAACCATGATCACA AGTGCAGA TTAATGTCTATGTACAAACACAGATGATATACACAGT CTAGTACA AACAGGGAAA | rs17561 | 7 (Minor Allele) 8 (Major Allele) |
| TAAAGAAATATGTTTTTAACAAGATTGAGGACTGGAT TATGAGGCTAGGG GAGGCTATCACAAACTGGAATAAAATAAAGCCAGAGA | rs3917356 chr2: 113308 494- | 9 (Minor Allele) 10 (Major Allele) |

TABLE 1 -continued

IL-1 Gene Cluster PI-Markers ([Minor allele/Major allele])

| Sequence | dbSNP accession no. | SEQ ID NO. |
|---|---|---|
| AAAGTGGCTGCNT<br>[C/T]<br>CCAACCTGCACAACTGACCTAGCTAGGCTGATGGCTG<br>GGCCNNCTAGGAA<br>GGCTACTGAGCATCATATAAAACAGAAGGGACAGCAG<br>GAATATAACATGG | 113308694 | |
| TAAGCCTCGTTATCCCATGTGTCNAAGAAGATAGGTT<br>CTGAAATGTGGAG<br>CACATGTTGTTTAGGTATAAAATCAGAAGGGCAGGCC<br>TCGTGAGGCGAGG<br>[T/C]<br>GGCAAAATTTGATTTCTTGGAGGACACCTGAGCATAT<br>ACGGTCAAAGTCT<br>GATGACAACACCAGTAGGGATGAAGCTGGGAGTGGGG<br>TGGCTAagaacac | rs1143633<br>chr2: 113306<br>598-<br>113306798 | 11 (Minor Allele)<br>12 (Major Allele) |
| TCTGTCTTCCAGACCACGTATGCTTTCCTCCACCTTT<br>GCATCTTTTATCT<br>TCTGCCAGCCCAGATGCTTGCTGACTCCAGCCCAAGC<br>CTATAGGATAAGC<br>[T/C]<br>ACAGCCTGTCCCTACAGACTACGCATTGCAGAATCTA<br>AGACATCAAGTCA<br>AGTTCGGAAGCACTTGCCTTCTCCTCTCCAGGTACAC<br>AGGCTCTCCTGGA | rs3917368<br>chr2: 113298<br>913-<br>113299113 | 13 (Minor Allele)<br>14 (Major Allele) |
| Ggattattccaaaaagagcctcaacatgcaggcgctt<br>attatNacttctc<br>ttgcatcatcctattggccaaagccagtcaNgtggct<br>aagtctagcccc<br>[T/C]<br>tgtgagaggagactNcataagagtgtgaacaccagga<br>gacacggtcactg<br>gggccaccactgtaaccatctaccacaGGACCTGAAT<br>CTCTGTGTGCTA | rs4252019 | 15 (Minor Allele)<br>16 (Major Allele) |
| ATGATCACAAGTGCAGATTAATGTCTATGTACAAACA<br>CAGATGATATACA<br>CAGTCTAGTACAAACAGGGAAAATAGTTCTGGAGGGG<br>NTATTAGGAATAT<br>[G/T]<br>CCAATCCAGATGAGGAAGCAAAGAGAAGTGAAATCAC<br>CCAGTCAGCAGAA<br>CTGGTTTTCTAGGATTATCCTTGTTGTTGCTTATGTG<br>CTTCTTTTTAAAC | rs2071374 | 17 (Minor Allele)<br>18 (Major Allele) | d. Detection

The PI-marker may be detected in a sample derived from the patient. Many methods are available for detecting a marker in a subject and may be used in conjunction with the herein described methods. These methods include large-scale SNP genotyping, exonuclease-resistant nucleotide detection, solution-based methods, genetic bit analyses, primer guided nucleotide incorporation, allele specific hybridization, and other techniques. Any method of detecting a marker may use a labeled oligonucleotide.

(1) Large Scale SNP Genotyping

Large scale SNP genotyping may include any of dynamic allele-specific hybridization (DASH), microplate array diagonal gel electrophoresis (MADGE), pyrosequencing, oligonucleotide-specific ligation, or various DNA "chip" technologies such as Affymetrix SNP chips. These methods may require amplification of the target genetic region. Amplification may be accomplished via polymerase chain reaction (PCR).

(2) Exonuclease-Resistant Nucleotide

PI-markers may be detected using a specialized exonuclease-resistant nucleotide, as described in U.S. Pat. No. 4,656,127, which is incorporated herein by reference. A primer complementary to the allelic sequence immediately 3' to the polymorphic site may be permitted to hybridize to a target molecule obtained from the subject. If the polymorphic site on the target molecule contains a nucleotide that is complementary to the particular exonuclease-resistant nucleotide derivative present, then that derivative may be incorporated onto the end of the hybridized primer. Such incorporation may render the primer resistant to exonuclease, and thereby permit its detection. Since the identity of the exonuclease-resistant derivative of the sample may be known, a finding that the primer has become resistant to exonuclease reveals that the nucleotide present in the polymorphic site of the target molecule was complementary to that of the nucleotide derivative used in the reaction. This method may not require the determination of large amounts of extraneous sequence data.

(3) Solution-Based Method

A solution-based method may be used to determine the identity of a PI-marker, as described in PCT Application No. WO91/02087, which is herein incorporated by reference. A primer may be employed that is complementary to allelic sequences immediately 3' to a polymorphic site. The method may determine the identity of the nucleotide of that site using labeled dideoxynucleotide derivatives that, if complementary to the nucleotide of the polymorphic site, will become incorporated onto the terminus of the primer.

(4) Genetic Bit Analysis

Genetic bit analysis may use mixtures of labeled terminators and a primer that is complementary to the sequence 3' to a polymorphic site. A labeled terminator may be incorporated, wherein it is determined by and complementary to, the nucleotide present in the polymorphic site of the target molecule being evaluated. The primer or the target molecule may be immobilized to a solid phase.

(5) Primer-Guided Nucleotide Incorporation

A primer-guided nucleotide incorporation procedure may be used to assay for a PI-marker in a nucleic acid, as described in Nyren, P. et al., Anal. Biochem. 208:171-175 (1993), which is herein incorporated by reference. Such a procedure may rely on the incorporation of labeled deoxynucleotides to discriminate between bases at a polymorphic site. In such a format, since the signal is proportional to the number of deoxynucleotides incorporated, polymorphisms that occur in runs of the same nucleotide may result in signals that are proportional to the length of the run.

(6) Allele Specific Hybridization

Allele specific hybridization may be used to detect a PI-marker. This method may use a probe capable of hybridizing to a target allele. The probe may be labeled. A probe may be an oligonucleotide. The target allele may have between 3 and 50 nucleotides around the marker. The target allele may have between 5 and 50, between 10 and 40, between 15 and 40, or between 20 and 30 nucleotides around the marker. A probe may be attached to a solid phase support, e.g., a chip. Oligonucleotides may be bound to a solid support by a variety of processes, including lithography. A chip may comprise more than one allelic variant of a target region of a nucleic acid, e.g., allelic variants of two or more polymorphic regions of a gene.

(7) Other Techniques

Examples of other techniques for detecting alleles include selective oligonucleotide hybridization, selective amplification, or selective primer extension. Oligonucleotide primers may be prepared in which the known mutation or nucleotide difference is placed centrally and then hybridized to target DNA under conditions which permit hybridization if a perfect match is found. Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

Allele specific amplification technology that depends on selective PCR amplification may be used in conjunction with the instant invention. Oligonucleotides used as primers for specific amplification may carry the mutation or polymorphic region of interest in the center of the molecule. Amplification may then depend on differential hybridization, as described in Gibbs et al. (1989) Nucleic Acids Res. 17:2437-2448), which is herein incorporated by reference, or at the extreme 3' end of one primer where, under appropriate conditions, mismatch can prevent, or reduce polymerase extension.

Direct DNA sequencing, either manual sequencing or automated fluorescent sequencing may detect sequence variation. Another approach is the single-stranded conformation polymorphism assay (SSCP), as described in Orita M, et al. (1989) Proc. Natl. Acad. Sci. USA 86:2766-2770, which is incorporated herein by reference. The fragments that have shifted mobility on SSCP gels may be sequenced to determine the exact nature of the DNA sequence variation. Other approaches based on the detection of mismatches between the two complementary DNA strands include clamped denaturing gel electrophoresis (CDGE), as described in Sheffield V C, et al. (1991) Am. J. Hum. Genet. 49:699-706, which is incorporated herein by reference; heteroduplex analysis (HA), as described in White M B, et al. (1992) Genomics 12:301-306, which is incorporated herein by reference; and chemical mismatch cleavage (CMC) as described in Grompe M, et al., (1989) Proc. Natl. Acad. Sci. USA 86:5855-5892, which is herein incorporated by reference. A review of currently available methods of detecting DNA sequence variation can be found in a review by Grompe (1993), which is incorporated herein by reference. Grompe M (1993) Nature Genetics 5:111-117. Once a mutation is known, an allele specific detection approach such as allele specific oligonucleotide (ASO) hybridization can be utilized to rapidly screen large numbers of other samples for that same mutation. Such a technique can utilize probes that may be labeled with gold nanoparticles to yield a visual color result as described in Elghanian R, et al. (1997) Science 277:1078-1081, which is herein incorporated by reference.

A rapid preliminary analysis to detect polymorphisms in DNA sequences can be performed by looking at a series of Southern blots of DNA cut with one or more restriction enzymes, preferably with a large number of restriction enzymes.

e. Amplification

Any method of detection may incorporate a step of amplifying the PI-marker. A PI-marker may be amplified and then detected. Nucleic acid amplification techniques may include cloning, polymerase chain reaction (PCR), PCR of specific alleles (ASA), ligase chain reaction (LCR), nested polymerase chain reaction, self-sustained sequence replication, transcriptional amplification system, and Q-Beta Replicase, as described in Kwoh, D. Y. et al., 1988, Bio/Technology 6:1197, which is incorporated herein by reference.

Amplification products may be assayed by size analysis, restriction digestion followed by size analysis, detecting specific tagged oligonucleotide oligonucleotide primers in reaction products, allele-specific oligonucleotide (ASO) hybridization, allele specific 5' exonuclease detection, sequencing, and/or hybridization.

PCR-based detection means may include amplification of a plurality of markers simultaneously. PCR primers may be selected to generate PCR products that do not overlap in size and may be analyzed simultaneously. Alternatively, one may amplify different markers with primers that are differentially labeled. Each marker may then be differentially detected. Hybridization-based detection means may allow the differential detection of multiple PCR products in a sample.

Nucleic acid primers and/or oligonucleotides may be used in conjunction with any of the herein described methods and/or kits. The following oligonucleotides or primers may be present in the herein described kits and/or used in the herein described methods:

TABLE 2

| SNP | Primer #1 | Primer #2 |
|---|---|---|
| IL1b_rs 1143639 | ACGTTGGATGAGACCTGTTCCCAGCTTC (SEQ ID NO: 19) | ACGTTGGATGCTCCTGCTACCACTTATTC (SEQ ID NO: 20) |
| IL1b_rs 1143634 | ACGTTGGATGGTGCTCCACATTTCAGAC (SEQ ID NO: 21) | ACGTTGGATGCAGTTCAGTGATCGTACAG (SEQ ID NO: 22) |
| IL1R1_rs 2228139 | ACGTTGGATGCTCCTGCAACGGGTAGTC (SEQ ID NO: 23) | ACGTTGGATGGTGCAAAATTTGTGGAGAG (SEQ ID NO: 24) |
| IL1a_rs 17561 | ACGTTGGATGTTTCACATTGCTCAGGAC (SEQ ID NO: 25) | ACGTTGGATGATCTGCACTTGTGATCATG (SEQ ID NO: 26) |
| IL1b_rs 1143633 | ACGTTGGATGTGACCGTATATGCTCAGG (SEQ ID NO: 27) | ACGTTGGATGATAAAATCAGAAGGGCAGC (SEQ ID NO: 28) |
| IL1RN_rs 4252019 | ACGTTGGATGGCTTGCATCATCCTATTC (SEQ ID NO: 29) | ACGTTGGATGCTGGTGTTCACACTCTTAG (SEQ ID NO: 30) |
| IL1a_rs 2071374 | ACGTTGGATGTGACTGGGTGATTTCACC (SEQ ID NO: 31) | ACGTTGGATGGGGAAAATAGTTCTGGAGG (SEQ ID NO: 32) |
| IL1b_rs 3917368 | ACGTTGGATGCTTTTATCTTCTGCCAGC (SEQ ID NO: 33) | ACGTTGGATGTGCAATGCGTAGTCTGTAG (SEQ ID NO: 34) |
| IL1b_rs 3917368 | ACGTTGGATGCTTTTATCTTCTGCCAGC (SEQ ID NO: 35) | ACGTTGGATGTGCAATGCGTAGTCTGTAG (SEQ ID NO: 36) |

A probe or oligonucleotide may comprise a SNP corresponding to rs1143639$^{256T}$ (as shown in SEQ ID NO:3), rs1143639$^{256C}$ (as shown in SEQ ID NO:4), rs1143634$^{401A}$ (as shown in SEQ ID NO:1), rs1143634$^{401G}$ (as shown in SEQ ID NO:2), rs2228139$^{301G}$ (as shown in SEQ ID NO:5), rs2228139$^{301C}$ (as shown in SEQ ID NO:6), rs17561$^{256A}$ (as shown in SEQ ID NO:7), rs17561$^{256C}$ (as shown in SEQ ID NO:8), rs3917356$^{256C}$ (as shown in SEQ ID NO:9), rs3917356$^{256T}$ (as shown in SEQ ID NO:10), rs1143633$^{401T}$ (as shown in SEQ ID NO:11), rs1143633$^{401C}$ (as shown in SEQ ID NO:12), rs3917368$^{301T}$ (as shown in SEQ ID NO:13), rs3917368$^{301C}$ (as shown in SEQ ID NO:14), rs4252019$^{501T}$ (as shown in SEQ ID NO:15), rs4252019$^{501C}$ (as shown in SEQ ID NO:16), and rs2071374$^{301G}$ (as shown in SEQ ID NO:17), rs2071374$^{301T}$ (as shown in SEQ ID NO:18). The probe or oligonucleotide may be a fragment of any one of SEQ NO:1 through SEQ NO:18, wherein the fragment comprises the corresponding SNP. The fragment may be between 10 and 500 nucleotides, between 50 and 400 nucleotides, between 100 and 300 nucleotides, between 200 and 250 nucleotides, between 10 and 50 nucleotides, between 10 and 20 nucleotides, between 10 and 30 nucleotides, or between 10 and 40 nucleotides in length.

3. Method of Treatment

In any patient that carries the PI-marker, an assessment may be made as to whether the subject is an early disease subject, wherein pulmonary infection has not occurred, or whether the subject has been colonized with a bacterial pathogen. The assessment may indicate an appropriate course of preventative or maintenance antibiotic therapy. Antibiotic therapy may be administered in different clinical settings during the life of a CF subject: (1) during early lung disease a subject may receive antibiotics to delay onset of chronic bacterial colonization; (2) after a subject has been colonized with one or more bacterial pathogens, wherein antibiotics may be administered to slow any decline in pulmonary function and reduce frequency and morbidity of pulmonary exacerbations; and/or (3) during periodic exacerbations in pulmonary symptoms, wherein intensive antibiotic regimens may be administered to relieve symptomatology and restore pulmonary function to baseline values.

a. Predictive Treatment

Provided herein is a method of treating a CF subject having a PI-marker. Antibiotics may be administered to the subject to prevent or delay onset of bacterial infection. The subject may be undergoing treatment for CF.

The treatment of a subject with a particular therapeutic may be monitored by determining protein, mRNA, and/or transcriptional level of a gene. The gene may be in the IL-1 gene cluster. The gene may be an IL-1α gene, IL-1β gene, IL-1 receptor gene, and/or IL-1 receptor antagonist gene. Depending on the level detected, the therapeutic regimen may be maintained or adjusted. The effectiveness of treating a subject with an agent may comprise (1) obtaining a preadministration sample from a subject prior to administration of the agent; (2) detecting the level or amount of a protein, RNA or DNA in the preadministration sample; (3) obtaining one or more post-administration samples from the subject; (4) detecting the level of expression or activity of the protein, RNA or DNA in the postadministration sample; (5) comparing the level of expression or activity of the protein, RNA or DNA in the preadministration sample with the corresponding protein, RNA, or DNA in the postadministration sample, respectively; and (6) altering the administration of the agent to the subject accordingly.

Cells of a subject may be obtained before and after administration of a therapeutic to detect the level of expression of genes other than the gene of interest to verify that the therapeutic does not increase or decrease the expression of genes that could be deleterious. Verification may be accomplished by transcriptional profiling. mRNA from cells exposed in vivo to a therapeutic and mRNA from the same type of cells that were not exposed to the therapeutic may be reverse transcribed and hybridized to a chip containing DNA from many genes. The expression of genes in the treated cells may be compared against cells not treated with the therapeutic.

b. Maintenance Therapy

Appropriate antibiotic therapy and/or anti-inflammatory therapy may be essential steps in the management of CF lung infection. Antibiotic selection for any given subject in any given setting may be based on periodic isolation and identification of pathogens from respiratory secretions and a review of the antimicrobial susceptibility profile for those pathogens. Antibiotics may be used for outpatient management of CF and/or for the treatment of bacteria associated with pulmonary exacerbations.

c. Antibiotics and Anti-Inflammatories

An antibiotic may be selected from the following: an aminoglycoside, amoxicillin, levofloxacin, dicloxacillin, cephalexin, amoxicillin/clavulanate, erythromycin, clarithromycin, azithromycin, clindamycin, cefuroxime axetil, cefprozil, cefixime, cefpodoxime proxetil, loracarbef, ciprofloxacin, tobramycin, colistin, trimethoprim/sulfamethoxazole, doxycycline, minocycline, cefazolin, nafcillin, vancomycin, β-lactam, ceftazidime, ticarcillin, piperacillin, imipenem, meropenem, aztreonam, an aminoglycoside, amikacin, merpenem, ceftazidime, chloramphenicol, ticarcillin/clavulanate, aztreonam, imipenem, a polypeptide antibiotic, and/or meropenem. The polypeptide antibiotic may be of the polymyxin class of antibiotics. A broad range antibiotic may be used in the regimen. A broad range antibiotic may include levofloxacin or amoxycillin.

An anti-inflammatory agent may be an IL-1 blocker. An IL-1 blocker may be selected from the following: rilonacept, anakinra, and/or Zn-protoporphyrin (ZnPP).

The antibiotic or anti-inflammatory may be formulated for administration by injection, inhalation or insufflation through the nose or mouth, or oral, buccal, parenteral, or rectal administration. The antibiotic or anti-inflammatory may be formulated for parenteral administration by injection, e.g., by bolus injection or continuous infusion. Formulations for injection may be presented in unit dosage form, e.g., in ampules or in multi-dose containers, with an added preservative. The antibiotic or anti-inflammatory may take such a form as a suspension, solution, or emulsion in oily or aqueous vehicles, and may contain formulating agents such as suspending, stabilizing and/or dispersing agents. Antibiotic or anti-inflammatory preparations for oral administration may be suitably formulated to give controlled release of the antibiotic. For buccal administration, the antibiotic may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant. In the case of a pressurized aerosol, the dosage unit may be determined by providing a valve to deliver a metered amount.

An effective dose of the antibiotic may be based upon a culture determination of the bacterial type causing the infection. In addition, an antimicrobial susceptibility report may indicate which families of antibiotic drugs are useful for the particular bacteria recovered from the infection. If the cause of the infection is unclear, but suspected to be due to bacteria, a broad-spectrum antibiotic may be prescribed for controlling a wide variety of bacterial types. In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. Therapeutically effective amounts of an antibiotic may range from approximately 0.05 mg to 10 g per kilogram body weight of the subject per day. Antibiotic use and dose regimens as they relate to pulmonary infections in CF subjects may be found in Gibson et al. (Pathophysiology and management of pulmonary infections in cystic fibrosis, Am. J. Respir. Crit. Care Med. 2003 Oct. 15; 168(8):918-51), which is incorporated by reference in its entirety.

4. Method of Monitoring CF

Also provided herein is a method of monitoring a CF subject for pulmonary infection. The CF subject may have been determined to have a predisposition for pulmonary infection. The CF subject may already have a pulmonary infection. It may be desirable to measure the effects of treatment on CF by treating the patient using a method comprising monitoring the lung infection. Monitoring for pulmonary infection, or progression of pulmonary infection, may include any pulmonary function test (PFT), microbial cultures, imaging techniques, inflammatory markers, serological markers, and any of several general signs such as exacerbation rate and nutritional status.

5. Kit

Provided herein is a kit, which may be used for diagnosing, monitoring, or treating a pulmonary infection. The kit may comprise a nucleic acid sample collecting means. The kit may also comprise a means for determining a marker in an IL-1 gene sequence, a nucleic acid for use as a positive control, and/or a nucleic acids sampling means. The nucleic sampling means may include substrates, such as filter paper, nucleic acid purification reagents, such as reaction buffer, polymerase, and dNTPs. Marker detection means may also be included in the kit. Such means may include, specific restriction enzymes, marker specific oligonucleotides, and degenerate oligonucleotide primers for PCR. The positive control may be used for sequence comparison.

The kit may also comprise one or more containers, such as vials or bottles, with each container containing a separate reagent. The kit may further comprise written instructions, which may describe how to perform or interpret an assay or method described herein.

The present invention has multiple aspects, illustrated by the following non-limiting examples.

EXAMPLES

Example 1

UNC and CWRU Study Populations

University of North Carolina and Case Western Reserve (UNC/CWRU) Cohort. For this case-control study, we used the DNA and serum samples from 840 patients with CF, enrolled from 44 centers, who were initially determined to be homozygous for the ΔF508 genotype. The diagnosis of CF was documented in the medical record by the pilocarpine iontophoresis sweat test (sweat chloride>60 mmol/L). The 840 patients initially enrolled were chosen because their $FEV_1$ measurements were in the lowest quartile or highest quartile for age among ΔF508 homozygotes; of these, the lung function of 275 patients was classified as severely impaired (lowest quartile) and that of 565 patients as mildly impaired (highest quartile). Quartiles were defined by the Cystic Fibrosis Foundation registry data classification of pulmonary function testing for the UNC center when compared to US CF centers allowing for CF-specific lung function classification. The $FEV_1$ measurement was obtained when the patient was clinically stable and not during a bronchitic exacerbation, defined as an $FEV_1$ change of greater than 15% predicted. A total of 32 patients were excluded because they had inadequate spirograms (2 patients), were found not to be homozygous for the ΔF508 genotype on a subsequent evaluation (8 patients), or did not achieve more than 90% probability of being congruent with others in the severe or mild category (22). There were 808 patients in the final data set. No patient was excluded because of race or ethnic background; 96.7% of the patients were identified as Caucasian.

Each patient received a unique code that allowed for de-identified data processing to maintain anonymity. Key phenotypic data were obtained from source documents, including pulmonary function reports and genotype. Spirometry was performed within this cohort, and the resultant forced expiratory curves were evaluated for acceptability, in accordance with current American Thoracic Society (ATS) recommendations. Because forced expiratory volume in 1 second (FEV1) is most predictive of survival in CF, it was used as the outcome for phenotype-genotype analysis. Spirometry and flow-volume loops were performed in compliance with ATS guidelines; values were recorded as both absolute value and percent predicted using standard reference equations. All values from spirometric testing were recorded in liters (L). Standard reference value equations were used to calculate percent of predicted for spirometric values adjusted for age.

Example 2

CHB Study Population

Children's Hospital Boston (CHB) Cohort. To attempt to replicate the results of the case-control study, we genotyped the SNPs in a second population of CF patients from CHB using a family-based design. All CF probands were registered in a clinical and laboratory database and followed at CHB from 1993 to 2005. The diagnosis of CF was documented in the medical record by the pilocarpine iontophoresis sweat test (sweat chloride>60 mmol/L) and/or the presence of 2 CFTR mutations. Over 90% of the CF patients were evaluated in the CF clinic at least once per year. The yearly visits were prospectively scheduled annualized visits where clinical evaluation was performed and laboratory data obtained to include pulmonary function testing, sputum culture and serum laboratory measures.

We evaluated 126 trios (ascertained by the proband) with a pulmonary phenotype similar to that used in the UNC/CWRU cohort. Forced expiratory volume in 1 second ($FEV_1$) was determined by standard spirometry, meeting American Thoracic Society criteria; absolute values were converted to a percentage of the predicted volume expected for a healthy individual of the same age, sex, and height on the basis of the regression equations. For each patient, we extracted all laboratory values and lung function test results from the medical record when the patient was at his or her stable baseline and not during a pulmonary exacerbation. A bronchitic exacerbation was defined as worsening of symptoms, as indicated by declining lung function and $FEV_1$ change of greater than 15% predicted, because such a decrease is a strong predictor of clinician-diagnosed pulmonary exacerbation.

We identified eligible CF patients and collected laboratory data from the clinical laboratory database at CHB. Specifically, for pulmonary function testing, microbiologic and genotype data were extracted and downloaded into an ORACLE database. A structured query language reporting tool was run to join the hospital-wide laboratory values requested to the CF patient population followed at CHB. In the CHB cohort, we had multiple laboratory and pulmonary function measurements spanning 13 years and were able to analyze the patients' PFT measurements in both categorical and longitudinal analyses. For the categorical lung function analysis, each patient's $FEV_1$ value was assigned a disease severity group based on $FEV_1$ values using the ESCF classification for patients in four age groups: 6-12 yrs (severe, $FEV_1 \leq 88.7\%$ predicted; moderate, >88.7-94.5%; mild >94.5-99.0%; very mild/normal, >99.0%); 13-17 yrs (severe, $FEV_1 \leq 76.5\%$ predicted; moderate, >76.5-81.1%; mild >81.1-87.7%; very mild/normal, >87.7%); 18-29 yrs (severe, $FEV_1 \leq 58.1\%$ predicted; moderate, >58.1-63.9%; mild >63.9-70.7%; very mild/normal, >70.7%); and >30 yrs (severe, $FEV_1 \leq 45.5\%$ predicted; moderate, >45.5-50.9%; mild >50.9-59.8%; very mild/normal, >59.8%). For the analysis, a child aged 12.9 would have an age of 12 because we used a "floor" statistical function that rounds the age down to the integer. CF patients in the very mild/normal and the mild severity group were pooled for analysis and compared to moderate and severe disease groups, which were also combined. Methods for ascertaining sputum culture in the CHB cohort included both deep throat and sputum cultures. Colonization was defined as one positive microbiologic growth on culture. Given the method for extracting data from various electronic sources and merging them, it was not possible to obtain symptom history or medication information. However, as Children's Hospital Boston is an accredited CF Care Center, patients received standard CF care as outlined by the CF Consortium guidelines. Approval by the Institutional Review Board was obtained, and we received informed consent from all subjects in the cohorts.

Example 3

SNP Genotyping and Association Analysis

We investigated the IL1-gene cluster on chromosome 2, based on the National Center for Biotechnology Information (NCBI) dbSNP build 125. We genotyped 58 SNPs in the IL-1 gene cluster in 808 CF subjects from UNC/CWRU cohort. SNPs in candidate genes were selected for genotyping on the basis of one of three criteria: $r.sup.2$ value of at least 0.7 (for linkage disequilibrium [LD]-tagging SNPs), allele frequency of at least 10% in European-American populations, and/or causing a non-synonymous alteration in the amino acid sequence of the coded protein. All SNPs were verified by review of documentation in three databases—dbSNP, the Innate Immunity (innate.immunity.net), and Seattle SNPs (pga.mbt.washington.edu) program for genomic applications (PGA) web sites. SNP genotyping was performed using the standard protocol for the iPLEX assay on a Sequenom MassARRAY MALDI-TOF mass spectrometer 26 (Sequenom, San Diego, Calif.) or TaqMan assays 27 (Applied Biosystems, Foster City, Calif.).

Single SNP association analyses were conducted using logistic regression for dichotomous outcomes and linear regression for continuous phenotypes. All population-based statistical analyses were performed using SAS statistical software (SAS Institute Inc., Cary, N.C.), while all family-based association testing was performed using FBAT 28 and PBAT. In the 2 cohorts, we evaluated a potential association between IL1 polymorphisms and lung function in CF in the following way. In the screening step, we tested for association between the selected SNPs and lung disease severity using extremes of pulmonary function measurements, as defined by Drumm and colleagues, in a case-control analysis in the UNC/CWRU CF subjects. In the replication cohort (CHB), we tested for association with affection status (an allele transmission distortion) as defined by the ascertainment of the proband in a family-based analysis, using the FBAT approach. As a secondary analysis, we also used the qualitative lung phenotype, with severity defined using extremes of pulmonary function measurement determined by ESCF classification, in a family-based analysis. Additionally, since quantitative lung function data were available in the CHB cohort, we evaluated the association between the selected SNPs and lung function in a longitudinal analysis, incorporating quantitative pulmonary function measurements over the first 5 study visits. Only the first five annualized study visits were included to minimize the number of missing subjects (data completeness >90% over the first 5 study visits) and minimize any potential cohort effect. The longitudinal analysis was conducted in SAS (version 9.1, Cary, N.C.) using a mixed model, with fixed effects for the SNP, subject age at baseline, and time under study. Random intercepts and slopes were modeled for each subject. In summary, we evaluated two CF populations (UNC/CWRU and CHB) and three phenotypes—analysis of extremes of lung function using dichotomized lung function severity (in UNC/CWRU and CHB cohorts), affection status/transmission distortion (CHB cohort), and longitudinal lung function measures (CHB cohort) to assess whether the IL-1 family gene cluster has an effect on CF lung disease.

Example 4

Associations Between IL-1 SNPs and Lung Function

A total of 808 UNC/CWRU subjects were analyzed. The mean age for 263 patients classified with severe lung disease was 16.2±4.1 years, and the mean age for 545 patients classified with mild lung disease was 28.6±9.7 years (Table 2). Males made up 49.4% of the severe disease group and 55.6% of the mild disease group. All of the analyzed patients were ΔF508 homozygous and therefore pancreatic-insufficient. Over 80% of the cohort had positive cultures for *P. aeruginosa*. The mean $FEV_1$% predicted was 46.6±16.1 in the severe group and 72.4±28.1 in the mild group. The rate of $FEV_1$ decline (percent/year) in the severe group was 3.65±2.20 and 1.35±1.51 in the mild group.

TABLE 2

| VARIABLE | SEVERE IMPAIRMENT (N = 263) | MILD IMPAIRMENT (N = 545) | P VALUE |
| --- | --- | --- | --- |
| AGE RANGE | 8-25 | 15-55 | |
| AGE MEAN | 16.2 +/- 4.1 | 28.6 +/- 9.7 | <0.001 |
| SEX (% MALE) | 49.4 | 55.6 | 0.10 |
| FEV1 (% OF PREDICTED VALUE) | 46.6 +/- 16.1 | 72.4 +/- 28.1 | <0.001 |
| FEV1 DECLINE (%/YEAR) | 3.65 +/- 2.20 | 1.35 +/- 1.51 | <0.001 |
| MEDIAN PREDICTED SURVIVAL | 31.4 | 56.6 | <0.001 |
| BODY-MASS INDEX (PERCENTILE) | 19.6 +/- 21.7 | 44.0 +/- 26.1 | <0.001 |
| POSITIVE TEST FOR *P. AERUGINOSA* (%) | 89.0 | 86.1 | 0.25 |
| DIABETES MELLITUS | 15.6 | 24.0 | 0.006 |
| ASTHMA | 19.4 | 22.0 | 0.39 |

In the replication cohort from CHB, a total of 126 trios were analyzed, with a mean age of 10 years±6.46 years for the CF patients when the first clinical values were analyzed (Table 3). This cohort was 53% male and 47% female. Forty-one percent of the patients were DF508 homozygous and 40% were heterozygotes. Ninety-five percent of the cohort was pancreatic-insufficient, and 92% had positive cultures for *P. aeruginosa*, of which 70% were positive for mucoid *P. aeruginosa*. The mean predicted rate of decline in $FEV_1$ was −2.29±3.76 (percent/year), consistent with an average decline in $FEV_1$ percent predicted of 2.5-2.6 (percent/year) for CF patients 31. Table 4 illustrates the pulmonary function data for the 126 CF subjects obtained at the first 5 clinical visits and stratified by age. In Table 4, there is a value for each subject per year. For example, if a subject had data each year from the age of 11-14, the subject was represented four times in the table. They were represented twice in the 6-12 age category and twice in the 13-17 age category.

TABLE 3

| | N | % | Mean | Min | Max |
| --- | --- | --- | --- | --- | --- |
| Trios | 126 | | | | |
| Female | 59 | 47 | | | |
| Age—at consent | 126 | | 18.5 +/- 8.7 | 8 | 45 |
| Age—on first clinical values | 126 | | 10.0 +/- 6.5 | 1 | 36 |
| 1-12 | 95 | 75 | | | |
| 13-17 | 17 | 13 | | | |
| 18-29 | 11 | 8 | | | |
| 30+ | 3 | 2 | | | |
| Genotype | | | | | |
| ΔF508 Homozygous | 52 | 41 | | | |
| ΔF508 Heterozygous | 51 | 40 | | | |
| Other | 15 | 12 | | | |
| Unknown | 8 | 6 | | | |
| Pancreatic Insufficient | 120 | 95 | | | |
| Sweat Chloride | 119 | 94 | 104.3 +/- 16.8 | 40 | 143 |
| FEV1 (% predicted) | 559 | | 92.9 +/- 19.6 | 24 | 162 |
| % change FEV1 %/yr | 559 | | -2.3 +/- 3.6 | -14.3 | 0 |

TABLE 4

| | Age and Number of Patient Visits(%)[b] | | | | |
| --- | --- | --- | --- | --- | --- |
| Disease Severity[a] | 6-12 | 13-17 | 18-29 | >30 yrs | Row Totals |
| Normal/very mild | 192(34%) | 53(9%) | 66(12%) | 17(3%) | 328(59%) |
| Mild | 48(9%) | 11(2%) | 6(1%) | 2(0%) | 67(12%) |
| Moderate | 38(7%) | 8(1%) | 1(0%) | 2(0%) | 49(9%) |

TABLE 4-continued

| | Age and Number of Patient Visits(%)[b] | | | | |
|---|---|---|---|---|---|
| Disease Severity[a] | 6-12 | 13-17 | 18-29 | >30 yrs | Row Totals |
| Severe | 96(17%) | 14(3%) | 4(1%) | 1(0%) | 115(21%) |
| Totals | 374(67%) | 86(15%) | 77(14%) | 22(4%) | 559(100%) |

[a]Each patient was assigned a disease assigned a disease severity group based on FEV1 values using the Epidemiological Study of Cystic Fibrosis (ESCF) classification for patients in four age groups: 6-12 yrs (severe, FEV1 ≤ 88.7% predicted; moderate, >88.7-94.5%; mild >94.5-99.0%; very mild/normal, >99.0%); 13-17 yrs (severe, FEV1 ≤ 76.5% predicted; moderate, >76.5-81.1%; mild >81.1-87.7%; very mild/normal, >87.7%); 18-29 yrs (severe, FEV1 ≤ 58.1% predicted; moderate, >58.1-63.9%; mild >63.9-70.7%; very mild/normal, >70.7%) and >=30 yrs (severe, FEV1 ≤ 45.5% predicted; moderate, >45.5-50.9%; mild >50.9-59.8%; very mild/normal, >59.8%).
[b]Excludes 47 visits for subjects when FEV1% predicted was missing.

We confined our analyses to self-described Caucasians to minimize the chance of identifying false associations due to population stratification in the case-control analysis. In addition, power to detect associations in other racial groups is low due to small sample sizes, particularly in CF, where the affected cohort is mostly Caucasian 32.

A total of 58 SNPs in the IL-1 gene cluster were initially investigated in the UNC/CWRU cohort; 9 SNPs were then investigated in the CHB cohort. Across both cohorts, none of the selected SNPs showed significant overall departure from Hardy Weinberg equilibrium. Genotyping quality for both Sequenom and TaqMan assays was high, with an average completion rate of 98%, no discordances on repeat genotyping of a random 10% of the cohort, and a low rate of Mendelian inconsistencies.

Analysis of extremes of lung function: We tested for an association between the selected SNPs and lung disease severity in subjects with "mild" (n=545) or "severe" (n=263) illness by Fisher's exact and Armitage trend testing. As shown in Table 5, three SNPs in the gene for IL1β (IL1B), rs1143633, rs1143639 and rs3917356, as well as a SNP in IL1-RN (the gene for the receptor antagonist for IL-1), rs4252019, were suggestive of an association with lung disease severity in CF (p<0.10). While not significant in the non-stratified analysis, when stratified by gender, other SNPs were associated with lung disease severity: another SNP, rs17561, in the gene for IL-1α (IL1A) (p<0.05 in the males), one SNP in the IL1B gene rs1143634 (p<0.07 in the females), and one SNP rs2228139 in the IL1-R1 gene (p<0.05 in the females). To further determine which SNPs to genotype in a family-based analysis, we fit a logistic regression model for each SNP, calculating the odds of severe versus mild CF for each genotype in all 58 SNPs initially screened by Fisher's exact and Armitage testing. The analysis with the logistic regression models confirmed the Armitage testing. Eight SNPs showed an OR>1.5 (rs17561, 3917356, 1143633, 1143634, 1143639, 3917368, 2228139, and 4252019), indicating a greater odds of having severe versus mild CF lung disease when comparing genotyping categories (data not shown). For an OR>1, the genetic variant is associated with disease and in this case worse pulmonary function. One SNP, rs2071374 in the gene for IL-1α (IL1A), had an OR≤0.5 indicating greater odds of having mild CF lung disease when comparing genotyping categories. With these promising results, we proceeded to evaluate 9 SNPs using a family-based analysis in a second population.

TABLE 5

Significant associations of IL-1 genotypes and mild (highest quartile*) versus severe (lowest quartile*) pulmonary function impairment in the UNC/CWRU cohort

| Gene | SNP Location | SNP rs# | MA | MAF (general population) | MAF (CF population) | Fisher's P Value | Fisher's P Value Male | Fisher's P value Female | Armitage P Value |
|---|---|---|---|---|---|---|---|---|---|
| IL1α | Intron 4 | 2071374 | G | 0.30 | 0.30 | 0.102 | 0.497 | 0.163 | 0.091 |
| IL1α | Exon 5 | 17561 | A | 0.33 | 0.29 | 0.415 | 0.008 | 0.015 | 0.248 |
| IL1β | Intron 3 | 3917356 | C | 0.43 | 0.47 | 0.093 | 0.290 | 0.306 | 0.035 |
| IL1β | Intron 4 | 1143633 | T | 0.45 | 0.38 | 0.067 | 0.329 | 0.157 | 0.073 |
| IL1β | Exon 5 | 1143634 | A | 0.25 | 0.23 | 0.120 | 0.350 | 0.069 | 0.064 |
| IL1β | Intron 6 | 1143639 | T | 0.28 | 0.23 | 0.057 | 0.289 | 0.039 | 0.038 |
| IL1β | 3'UTR | 3917368 | T | 0.46 | 0.38 | 0.109 | 0.523 | 0.125 | 0.105 |
| IL1R1 | Exon 4 | 2228139 | G | 0.11 | 0.07 | 0.186 | 1.0 | 0.035 | 0.057 |
| IL1RN | Intron 4 | 4252019 | T | 0.09 | 0.14 | 0.048 | 0.572 | 0.005 | 0.015 |

With respect to Table 5, SNP rs #-refSNP number, MA means minor allele, MAF means minor allele frequency in the general and CF populations, and p is the p-value obtained from linear regression under an additive model using Fisher's and Armitage testing. * Quartiles are based on the ESCF classification of pulmonary function testing for the UNC/CWRU center when compared to US CF centers 19. For the UNC/CWRU case-control data, p-values were obtained from a Fisher's exact test and Armitage trend comparing genotype counts in cases (severe CF) to controls (mild CF). There is an overtransmission of the minor allele in the severe CF cases for these SNPs.

Example 5

Analysis of Extremes of Lung Function in UNC/CWRU Cohort

SNP characteristics (allele frequency and Hardy-Weinberg equilibrium) for each SNP were assessed. Selected SNPs in candidate genes were genotyped in 808 ΔF508 homozygotes with "severe" or "mild" lung disease, as defined by the lowest or highest quartile of forced expired volume (FEV1) for age. We tested for association between the selected SNPs and lung disease severity in subjects with "mild" (n=545) and "severe" (n=263) illness by both Fisher's exact and Armitage trend testing. Multivariable associations between individual SNP and $FEV_1$ percent predicted in the presence of potential confounders (age and gender) were tested using a general linear model. Genotypes were coded assuming an additive genetic model. For complex trait statistical models in which 2 or more loci may be involved in disease susceptibility, additive models, in which the allele-specific risks of disease are associated with the multilocus genotypes across different loci, can be modeled as sums of factors for each genotype at each locus. Odds ratios comparing severe versus mild CF were also calculated for each genotype (with the homozygote wild-type as the reference group) for all 58 SNPs, to determine whether significant Fisher's exact and Armitage tests corresponded to a clinically meaningful change in the odds of severe CF. The Fisher's test was conducted to assess the magnitude of effect and examine the effect of each genotyped on risk, without imposing any assumptions about the genetic model. From these analyses, 9 SNPs with OR≤0.5 or >1.5 showing evidence of association and moderate effect sizes were selected for further testing in subjects recruited from Children's Hospital Boston.

Example 6

Analysis of Extremes of Lung Function in CHB Cohort

For the familial data (CHB), 9 SNPs were tested using an additive model for evidence of association with the diagnosis of CF in the proband. The purpose was to determine whether any of the SNP alleles were significantly over- or under transmitted to the proband.

Analysis of extremes of lung function in CHB cohort: We tested for association between the selected SNPs and lung disease severity in subjects with "mild" or "severe" illness as defined by an assigned disease severity group, based on $FEV_1$ values and using the ESCF patient classification for patients (described in methods). Due to the small sample size in the CHB cohort, we were unable to analyze on the subjects in either of the "extreme" categories of normal/mild or moderate/severe lung impairment. Thus, the ESCF classification was collapsed into two categories: normal/mild and moderate/severe. In the CHB family analysis, p-values were obtained from an FBAT statistic comparing observed to expected allele transmission from parents to CF probands with normal/mild or moderate/severe lung function impairment at the first study visit.

Longitudinal analysis of $FEV_1\%$ predicted in the CHB cohort: Longitudinally measured lung function phenotypes were available in this cohort. As some of the associations observed in the UNC/CWRU cohort displayed differential effects by gender, both overall and gender-stratified analyses were conducted.

To maximize the power to detect an association, we analyzed percent-predicted $FEV_1$ with a multivariate population-based analysis (the offspring genotype, rather than parent-child allele transmissions, was the predictor of interest). A mixed model (SAS, Cary N. C.) was fit, including a random effect for each subject and for time since recruitment. Each SNP was tested separately, assuming either an additive, dominant or recessive genetic model as a fixed effect, along with age at recruitment, gender, and time since recruitment. As ΔF508 polymorphisms in the CFTR gene are the most common cause of CF, the analysis was repeated with adjustment for the presence or absence of 2 copies of ΔF508 alleles using a recessive genetic model.

Finally, we examined the relationship between the two SNPs of interest, rs1143634 and rs1143639, and the presence of non-mucoid or mucoid *P. aeruginosa* in the CHB cohort. Methods for ascertaining culture included both deep throat and sputum cultures. Colonization was defined as one positive microbiologic growth on culture. Two sets of analyses were conducted. Initially, logistic regression models were fit to determine whether rs1143634 or rs1143639 genotypes predicted the presence or absence of non-mucoid or mucoid *P. aeruginosa*, after adjusting for age at first study visit. Second, survival analyses (also adjusting for age at first study visit) were performed to test whether specific rs1143634 or rs1143639 genotypes predicted time of onset of non-mucoid or mucoid *P. aeruginosa*. The analysis was conducted using a Cox-proportional hazards model was fit (using proc phreg in SAS) to test this hypothesis in both the overall group and gender-stratified groups.

Affection status analysis (transmission distortion): We next evaluated 126 trios in a second population of CF patients from CHB using a family-based design. Due to the gender-specific differences observed for SNPs selected from the UNC/CWRU sample for replication, the association analysis of affection status in the CHB cohort was conducted in both the overall and gender-stratified cohort. Under an additive model, two of the SNPs associated with the IL1B gene, rs1143634 and rs1143639, were suggestive of an association in the gender-stratified analysis (p<0.05). None of the other 7 SNPs was nominally significant (all p>0.05) in either the overall or stratified cohort.

As shown in Table 6, in the subgroup analysis, the p-values for the females is significant (p<0.05), demonstrating a strong effect size, given the small number of informative trios in the CHB cohort (the number of informative trios for females was 29 for both SNPs). The direction of the association is consistent across the UNC/CWRU and CHB cohorts; the frequency of the minor allele is overrepresented in the UNC/CWRU severe CF cases (Table 5) and overtransmitted to female probands in the CHB cohort (Table 6). Therefore, the association is suggestive, given the consistency across studies and the relatively small number of female subjects (n=366 in UNC/CWRU and informative trios=29 in CHB), and p-values (p<0.10).

TABLE 6

Analysis of Affection Status in Children's Boston Cohort

| | | Females | | Males | | Overall | |
|---|---|---|---|---|---|---|---|
| SNP | Minor Allele | N info. families | Nominal 2-sided p-value | N info. families | Nominal 2-sided p-value | N info. families | Nominal 2-sided p-value |
| rs1143634 | A | 29 | 0.016 | 43 | 0.285 | 66 | 0.463 |
| rs1143639 | T | 29 | 0.016 | 42 | 0.225 | 65 | 0.527 |

With respect to Table 6, P-values were obtained from an FBAT statistic comparing observed versus expected (assuming Mendelian) transmission from parents to affected offspring. All probands in this analysis have CF. In females the minor allele for both SNPs is overtransmitted (p=0.016).

Given the consistent association in females, the p-values for rs1143634 and rs1143639 from Fisher's test of association in the UNC/CWRU cohort and p-values from the family-based association test in the CHB cohort were combined using Fisher's combined probability test 33. The joint p-values for SNPs rs 1143634 and rs1143639 from the overall test of association for the two studies, as well as the analysis in males, were not significant. For females, the unadjusted joint p-values were 0.0086 and 0.0052 in rs 1143634 and rs1143639, respectively. After a false discovery rate (FDR) correction was applied to the UNC/CWRU cohort, accounting for the 58 SNPs initially tested 34, the adjusted p-values were 0.059 (rs 1143634) and 0.052 (rs1143639).

Analysis of extremes of lung function in the CHB cohort: We also evaluated a dichotomous phenotype in the CHB cohort, based on FEV1 ESCF categories, similar to the categorization of the UNC/CWRU cohort. To maximize information from an increased sample size that has fewer quantitative measures, the UNC/CWRU analysis compared extremes of lung function, that is, severely impaired (lowest quartile) with mildly impaired (highest quartile). For the CHB family data, which are from a smaller sample than the UNC/CWRU cohort but include additional longitudinal quantitative $FEV_1$ measurements, p-values were obtained from an FBAT statistic comparing observed to expected allele transmission from parents to CF probands with collapsed ESCF categories of normal/mild or moderate/severe lung function impairment. There was no association in either the overall or gender-stratified analysis in the CHB cohort (data not shown). However, this may be due to the small sample size, particularly in the gender-stratified analysis. The number of informative families in each analysis ranged from 55 (in the overall analysis) to 24 (in the gender-stratified analysis for females).

Longitudinal analysis of $FEV_1\%$ predicted in the CHB cohort: To extract the most information from our cohort, we also conducted a population-based longitudinal analysis. Due to the unavailability of longitudinal lung function data in the UNC/CWRU cohort, additional analyses of lung function could be conducted only in the CHB cohort. The two SNPs of interest in the IL1B gene from the affection status analysis, rs1143634 and rs1143639, were tested for association using the $FEV_1\%$ predicted phenotype, measured at the first 5 study visits.

Figure 2:
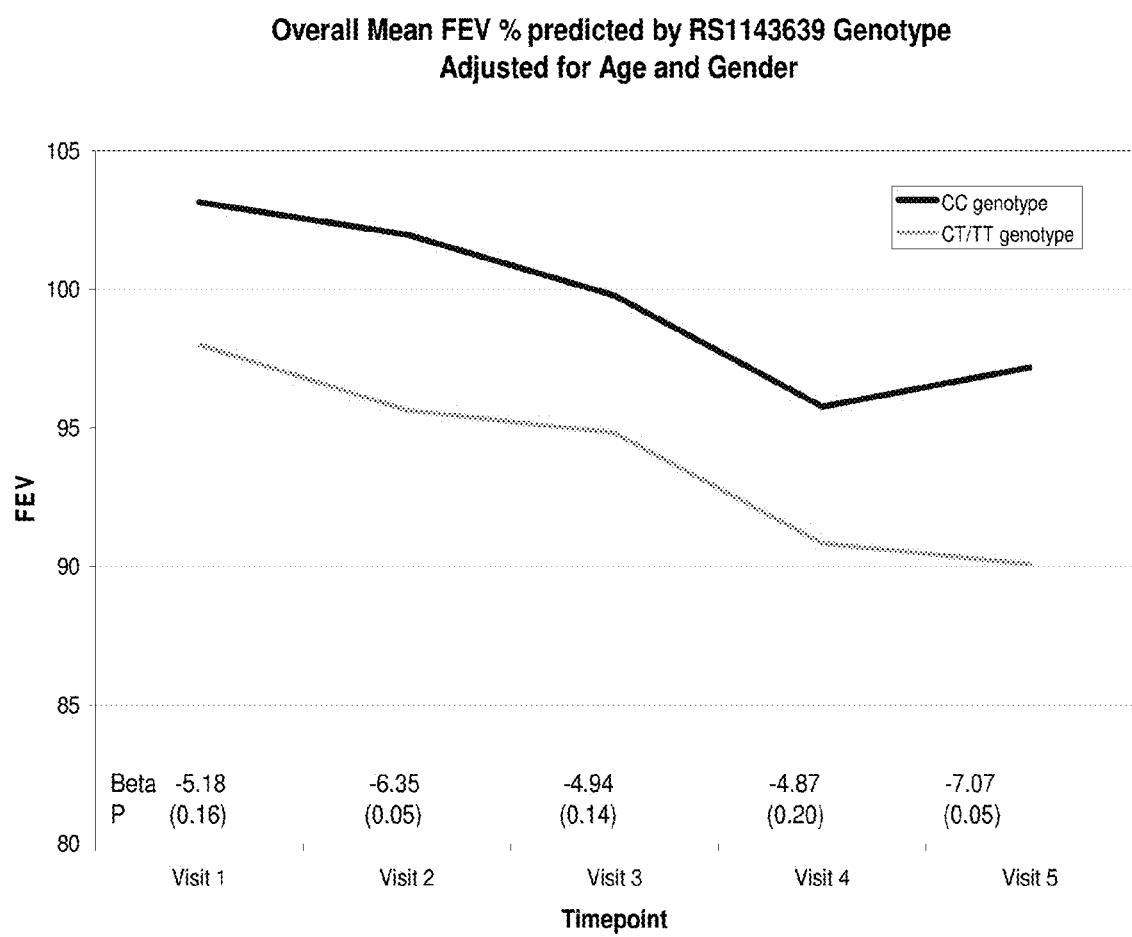
FIG. 2 shows the overall mean FEV % predicted by rs1143639 genotype as adjusted for age and gender.

FIGS. 1 and 2 present the age- and gender-adjusted means for FEV1% predicted for each genotype for IL1B SNPs rs1143634 and rs1143639. In FIG. 1, 56 patients are homozygous major for the GG genotype, and 43 are heterozygous/homozygous minor with either AG or AA genotype. In FIG. 2, 57 patients are homozygous for the major allele, CC and 42 patients are heterozygous/homozygous minor for the CT or TT genotype. The average length of time from the first study visit to the second study visit was 1.4 years, and the mean length of time between subsequent visits was one year. The mean length of time over all 5 of the study visits was 4.5 years. The calculated means are limited to subjects with complete data for the first 5 study visits, to limit any potential cohort effects. Displayed above each study visit (on the x-axis) are the corresponding univariate effect size estimates and p-values for each genotype group. There is a difference in the $FEV_1\%$ predicted in subjects with one or two copies of the minor A or T allele for rs1143634 or rs1143639, respectively.

In the overall group, for rs1143634, the mean difference in $FEV_1$ between the GG and AG/AA genotype groups across the five study visits was 5.6%, after adjusting for age and gender. For rs1143639, the mean difference in $FEV_1$ between the CC and CT/TT genotype groups across the five study visits was 6.7%, after adjusting for age and gender. We would expect similar results for these two SNPs, because the linkage disequilibrium (LD) between the two markers is similar (D=−0.171, D'=1.0 and R2=0.98). The longitudinal model adjusted for age at the first visit as well as time in follow-up, to reflect the variable ages and to account for the effect of age on $FEV_1$. Age was not significant across the different genotype groups. We also analyzed the means by genotype (homozygote major allele versus heterozygote and homozygote minor combined) and t-tests of the difference in ages (at each study visit) across groups. None of the differences was significant (data not shown).

Table 7 presents the multivariate results for the dominant model, adjusting for age and gender in the overall group, and for age in the gender-stratified analysis. There is a trend toward decreasing $FEV_1\%$ predicted for the heterozygote or homozygote minor allele. The overall p-value (a test of whether the mean $FEV_1\%$ predicted differs across the major allele homozygotes versus the heterozygotes and minor allele homozygotes combined) was 0.06 for SNP rs1143634 and 0.05 for SNP rs1143639. Therefore, in the longitudinal analyses, having one or two copies versus none of the minor allele shows evidence of association (p<0.10) for both of the SNPs within the IL1B gene and lung function decline. The analysis of the CHB cohort was repeated with adjustment for ΔF508 alleles, assuming a recessive genetic model. The presence of ΔF508 mutations was not associated with $FEV_1\%$ predicted and did not affect the relationship between SNPs rs1143634 or rs1143639 and $FEV_1\%$ predicted. The magnitude of the effect size estimates and p-values for SNPs rs1143634 and rs1143639 did not substantially change after inclusion of ΔF508 in the model (data not shown).

TABLE 7

| | Population-based Analysis for a mean decrease in FEV1 % predicted | | | |
|---|---|---|---|---|
| Time point | RS1143634 (AG/AA vs. GG) | | RS1143639 (CT/TT vs CC) | |
| All 5 visits | Beta | p | Beta | p |
| Female | −7.21 | 0.06 | −7.05 | 0.06 |
| Male | −3.29 | 0.32 | −4.10 | 0.29 |
| Overall | −5.17 | 0.06 | −5.27 | 0.05 |

With respect to table 7, all analyses are adjusted for age. Overall analysis is also adjusted for gender. The overall p values test whether mean $FEV_1\%$ predicted differs across the major allele homozygotes versus the heterozygotes and minor allele homozygotes combined.

Finally, we examined the relationship between the two IL1B-associated SNPs of interest, rs1143634 and rs1143639, and the presence of non-mucoid or mucoid *P. aeruginosa*. Neither the logistic regression analyses nor the Cox model showed a relationship between rs1143634 or rs1143639 genotypes and the presence or onset of mucoid *Pseudomonas* (data not shown). There was no significant association between the SNPs and presence of non-mucoid *P. aeruginosa*. However, in the overall (non-stratified analysis), for both rs1143634 and rs1143639, the presence of one or two copies of the minor allele was associated with a later onset of non-mucoid *P. aeruginosa*, with hazard ratios of 0.624 and 0.661, and p-values of 0.039 and 0.068, respectively.

We claim:

1. A method of treating a pulmonary infection in a human subject with a pulmonary infection marker, comprising:
   detecting a pulmonary infection marker in a sample from the subject, wherein the detection of the marker comprises:
   (a) providing a nucleic acid-containing sample obtained from the subject;
   (b) amplifying a nucleic acid comprising the marker; and
   (c) detecting the amplified nucleic acids, thereby detecting the marker,
   wherein the pulmonary infection marker is selected from the group consisting of SEQ ID NO:3, SEQ ID NO:1, SEQ ID NO:5, SEQ ID NO:7 and SEQ ID NO:15; and
   administering an anti-inflammatory agent or antibacterial agent to the subject in which the pulmonary infection marker is detected, thereby treating the pulmonary infection in the subject.

2. The method of claim 1, wherein the anti-inflammatory is an IL1 blocker.

3. The method of claim 2, wherein the IL1 blocker is selected from the group consisting of rilonacept, anakinra, and Zn-protoporphyrin (ZnPP).

4. The method of claim 1, wherein the pulmonary infection is associated with bacterial lung colonization.

5. The method of claim 4, wherein the bacterium is selected from the group consisting of P. aeruginosa, S. aureus, H. influenae, B. cepacia, methicillin-resistant S. aureus, S. maltophilia, and A. xylosoxidans.

6. The method of claim 1, wherein the marker is detected by sequencing.

7. The method of claim 1, wherein the marker is amplified using a pair of primers comprising the sequences selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:29 and SEQ ID NO:30.

8. The method of claim 7, wherein the amplified nucleic acids are detected by hybridizing an oligonucleotide probe to the amplified product.

9. The method of claim 8, wherein the probe is labeled with a detectable label.

10. The method of claim 8, wherein the probe is an oligonucleotide comprising a SNP selected from the group consisting of SEQ ID NO:3, SEQ ID NO:1, SEQ ID NO:5, SEQ ID NO:7 and SEQ ID NO:15.

11. The method of claim 1, wherein the presence of a marker selected from the group consisting of SEQ ID NO:11, SEQ ID NO:15, and SEQ ID NO:3 is diagnostic of the subject having a predisposition for severe pulmonary infection.

12. The method of claim 1, wherein the pulmonary infection marker indicates that the subject has a predisposition for pulmonary infection.

* * * * *